United States Patent
Accisano, III et al.

(10) Patent No.: US 7,824,367 B2
(45) Date of Patent: *Nov. 2, 2010

(54) DRAINAGE CATHETER WITH LOCKING HUB

(75) Inventors: Nicholas Gerald Accisano, III, Howell, NJ (US); Fred Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 1224 days.

This patent is subject to a terminal disclaimer.

(21) Appl. No.: 11/205,609

(22) Filed: Aug. 17, 2005

(65) Prior Publication Data

US 2007/0078385 A1    Apr. 5, 2007

(51) Int. Cl.
*A61M 31/00* (2006.01)
*A61M 37/00* (2006.01)
*A61M 27/00* (2006.01)

(52) U.S. Cl. .................... 604/95.04; 604/541
(58) Field of Classification Search ............. 604/95.04, 604/93.01, 95.05, 95.01, 541; 600/144–149
See application file for complete search history.

(56) References Cited

U.S. PATENT DOCUMENTS

| | | |
|---|---|---|
| 604,617 A | 5/1898 | Hoxie |
| 1,207,479 A | 12/1916 | Bisgaard |
| 2,051,247 A | 8/1936 | De Haes |
| 3,315,592 A | 4/1967 | Lems |
| 3,513,848 A | 5/1970 | Winston et al. |
| 3,798,687 A | 3/1974 | Stevens |
| 3,924,633 A | 12/1975 | Cook et al. |
| 4,206,910 A | 6/1980 | Biesemeyer |
| 4,573,981 A | 3/1986 | McFarlane |
| 4,586,923 A * | 5/1986 | Gould et al. ............. 604/95.04 |

(Continued)

FOREIGN PATENT DOCUMENTS

WO    WO2006/098818    9/2006

(Continued)

OTHER PUBLICATIONS

Office action dated May 28, 2008 in U.S. Appl. No. 11/078,140.

(Continued)

*Primary Examiner*—Kevin C Sirmons
*Assistant Examiner*—Andrew M Gilbert
(74) *Attorney, Agent, or Firm*—Stoel Rives LLP

(57) ABSTRACT

A drainage catheter hub for use in connection with a drainage catheter to receive and secure a suture therein, wherein the hub includes: (i) a housing having a channel to accommodate the suture therein; (ii) a bistable locking mechanism positioned in the housing and being adapted to provide selective securement of the suture; and (iii) a resilient outer layer utilized in connection with the bistable locking mechanism and coupled to the housing. The bistable locking mechanism is configured to: (i) allow movement of the suture when the bistable locking mechanism is in a first position; and (ii) minimize axial movement of the suture when the bistable locking mechanism is in a second position. The resilient outer layer is adapted to allow a user to actuate the bistable locking mechanism between the first and second positions to selectively secure and release the suture.

14 Claims, 4 Drawing Sheets

U.S. PATENT DOCUMENTS

| | | | |
|---|---|---|---|
| 4,643,720 A | 2/1987 | Lanciano | |
| 4,738,667 A | 4/1988 | Galloway | |
| 4,740,195 A * | 4/1988 | Lanciano | 604/533 |
| 4,787,892 A | 11/1988 | Rosenberg | |
| 4,885,503 A | 12/1989 | Takahashi et al. | |
| 5,052,998 A | 10/1991 | Zimmon | |
| 5,074,484 A | 12/1991 | Kray | |
| 5,078,684 A | 1/1992 | Yasuda | |
| 5,213,575 A | 5/1993 | Scotti | |
| 5,224,935 A | 7/1993 | Hollands | |
| 5,308,318 A | 5/1994 | Plassche, Jr. | |
| 5,352,198 A | 10/1994 | Goldenberg et al. | |
| 5,399,165 A * | 3/1995 | Paul, Jr. | 604/95.04 |
| 5,419,764 A | 5/1995 | Roll | |
| 5,472,435 A | 12/1995 | Sutton | |
| 5,489,269 A | 2/1996 | Aldrich et al. | |
| 5,522,400 A | 6/1996 | Williams | |
| 5,549,331 A | 8/1996 | Yun et al. | |
| 5,666,970 A | 9/1997 | Smith | |
| 5,693,083 A | 12/1997 | Baker et al. | |
| 5,707,926 A | 1/1998 | Frisch et al. | |
| 5,730,724 A * | 3/1998 | Plishka et al. | 604/95.04 |
| 5,730,730 A | 3/1998 | Darling, Jr. | |
| 5,806,202 A | 9/1998 | Blackman et al. | |
| 5,893,880 A | 4/1999 | Egan et al. | |
| 5,904,648 A | 5/1999 | Arndt et al. | |
| 5,941,849 A | 8/1999 | Amos, Jr. et al. | |
| 6,159,177 A * | 12/2000 | Amos et al. | 604/95.04 |
| 6,165,183 A | 12/2000 | Kuehn et al. | |
| 6,213,986 B1 | 4/2001 | Darling, Jr. | |
| 6,231,542 B1 | 5/2001 | Amos et al. | |
| 6,358,271 B1 | 3/2002 | Egan et al. | |
| 6,454,740 B1 | 9/2002 | Mody | |
| 6,508,789 B1 * | 1/2003 | Sinnott et al. | 604/164.02 |
| 6,547,761 B2 | 4/2003 | Liu | |
| 6,673,060 B1 | 1/2004 | Fleming, III | |
| 6,699,233 B2 * | 3/2004 | Slanda et al. | 604/533 |
| 6,997,951 B2 * | 2/2006 | Solem et al. | 623/2.37 |
| 7,087,038 B2 * | 8/2006 | Lee | 604/95.04 |
| 7,217,256 B2 | 5/2007 | Di Palma | |
| 7,338,475 B2 | 3/2008 | Brown | |
| 7,578,814 B2 | 8/2009 | Accisano et al. | |
| 7,641,630 B2 | 1/2010 | Accisano, III et al. | |
| 2004/0059293 A1 | 3/2004 | Chu et al. | |
| 2005/0070821 A1 | 3/2005 | Deal et al. | |
| 2005/0107739 A1 | 5/2005 | Di Palma | |
| 2005/0203485 A1 | 9/2005 | Lee | |
| 2006/0129111 A1 | 6/2006 | Mottola | |
| 2006/0206096 A1 | 9/2006 | Accisano et al. | |
| 2006/0212009 A1 | 9/2006 | Accisano et al. | |
| 2006/0217667 A1 | 9/2006 | Accisano et al. | |
| 2007/0032779 A1 | 2/2007 | Accisano et al. | |
| 2007/0083189 A1 | 4/2007 | Lampropoulos | |
| 2008/0097394 A1 | 4/2008 | Lampropoulos | |

FOREIGN PATENT DOCUMENTS

| | | |
|---|---|---|
| WO | WO2006/098819 | 9/2006 |
| WO | WO2006/101592 | 9/2006 |
| WO | WO2007/019074 | 2/2007 |

OTHER PUBLICATIONS

Office action dated Mar. 3, 2009 in U.S. Appl. No. 11/078,140.
Notice of allowance dated Oct. 13, 2009 in U.S. Appl. No. 11/078,140.
International search report and written opinion for PCT/US2006/003464 dated Jul. 26, 2007.
Office action dated Sep. 4, 2008 in U.S. Appl. No. 11/198,642.
Notice of allowance dated Apr. 20, 2009 in U.S. Appl. No. 11/198,642.
Issue notification dated Aug. 5, 2009 in U.S. Appl. No. 11/198,642.
International search report and written opinion for PCT/US2006/029304 dated Feb. 21, 2007.
Office action dated Mar. 10, 2009 in U.S. Appl. No. 11/081,301.
Office action dated Jun. 26, 2008 in U.S. Appl. No. 11/081,301.
Office action dated Oct. 23, 2007 in U.S. Appl. No. 11/081,301.
Office action dated Oct. 16, 2008 in U.S. Appl. No. 11/608,518.
Notice of allowance dated Jul. 27, 2009 in U.S. Appl. No. 11/608,518.
Notice of allowance dated Feb. 5, 2010 in U.S. Appl. No. 11/608,518.
International search report and written opinion for PCT/US2006/003021 dated Sep. 18, 2007.
Notice of allowance dated Aug. 5, 2009 in U.S. Appl. No. 11/078,939.
Office action dated May 21, 2008 in U.S. Appl. No. 11/078,939.
Notice of allowance dated Jan. 26, 2010 in U.S. Appl. No. 11/078,939.
International search report and written opinion for PCT/US2006/003467 dated Jun. 14, 2006.
Office action dated May 6, 2009 in U.S. Appl. No. 11/507,777.
Office action dated Sep. 9, 2009 in U.S. Appl. No. 11/507,777.
Notice of abandonment dated Dec. 1, 2009 in U.S. Appl. No. 11/081,301.
'Angiodynamics, Abscession Drainage Catheter: A Quick Guide to the Locking Mechanism.' AngioDynamics, Inc., Nov. 1999.
Office action dated Jul. 14, 2010 in U.S. Appl. No. 12/557,348.

* cited by examiner

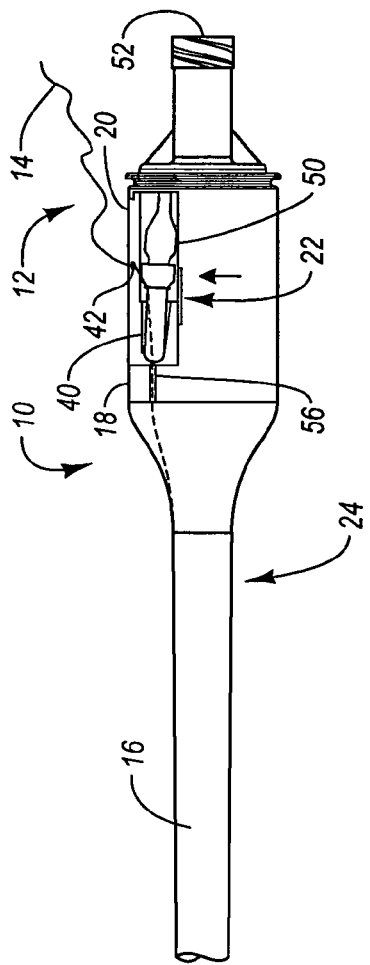
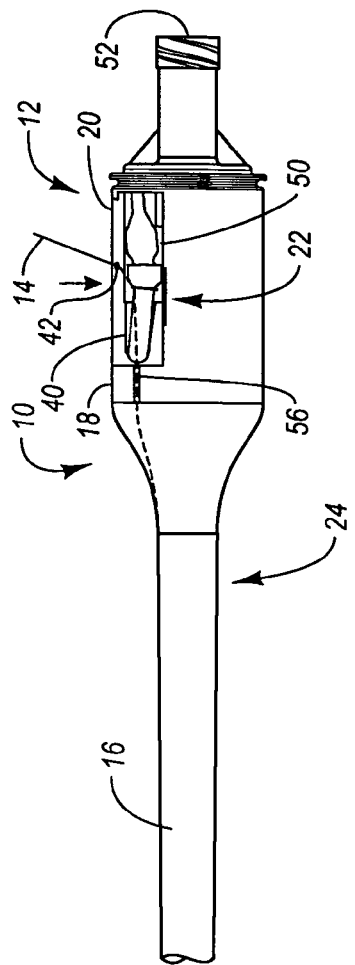
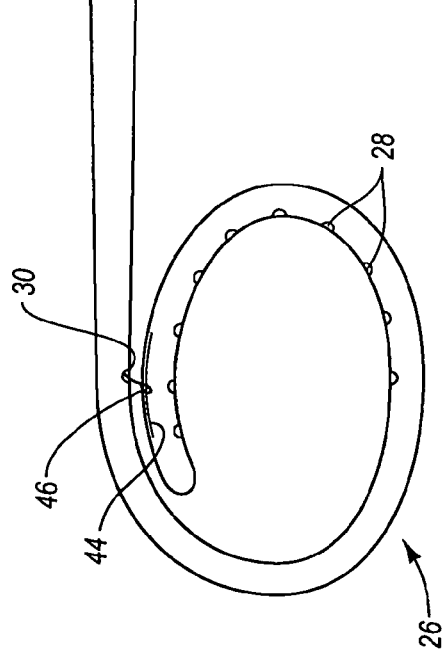
Fig. 1A
Fig. 1B

DRAINAGE CATHETER WITH LOCKING HUB

BACKGROUND OF THE INVENTION

1. The Field of the Invention

This invention relates to systems and apparatus for draining bodily fluid from a patient. In particular, the present invention relates to drainage catheters, and more specifically, to a drainage catheter hub apparatus for selectively securing or releasing a suture.

2. Background and Relevant Art

Drainage catheters are used in a variety of medical settings for draining fluids from a patient's body. For example, a patient may suffer an injury, or have a medical condition where a bodily tissue stores an excess amounts of fluid, such as blood, or other bodily serum. If the fluid is not removed further complications in the patient can occur such as rupturing or infection of the tissue. Accordingly, drainage catheters have been developed to remove these fluids from the patient, to either relieve pressure, or to otherwise ensure the fluid build up does not result in tissue injury.

Conventional drainage catheters typically comprise a hub, an elongate catheter tube communicatively connected to the hub, and a flexible tip that includes a plurality of drainage bores. The drainage bores of the flexible tip allow communication of fluid through the elongate catheter tube. The practitioner inserts the tip and catheter tube into the patient's body, such that the tip enters the tissue or area of fluid build up. The user then pulls a suture, which extends from the hub, passes along the length of the catheter tube, and is secured to the tip. When the practitioner pulls or retracts the suture, the tip flexes inward toward the catheter tube, thereby forming a curved loop having drainage bores within the fluid build up area.

To hold the suture in place in order to maintain the curved configuration of the catheter tube, the practitioner either must hold the suture and catheter with two hands, or secure the suture to the catheter hub by wrapping the suture around the hub. Unfortunately, securing the catheter hub in this manner can be somewhat insecure and inconvenient, especially if the catheter is to remain in place for an extended period of time. In the event that additional manipulation or repositioning of the catheter tube must be utilized, it can be difficult to unwrap the suture from the hub for proper manipulation of the length of catheter.

Once the tip of the catheter tube is appropriately positioned, the excess fluid then flows into the individual drainage bores of the tip, flows along the length of the catheter tube, and is drained from the catheter hub. Thereafter, the practitioner will remove the catheter from the localized area. Unfortunately, the curved conformation of the tip relative to the catheter tube makes it difficult to remove the drainage catheter from its drainage position. In particular, removing the drainage catheter while the tip is still in an inwardly flexed position can cause the drainage catheter to tear or otherwise damage bodily tissue. Accordingly, the practitioner typically attempts to straighten the tip before removing the catheter. Generally, this requires at a minimum releasing the suture that caused the tip to flex in the first instance. Where the suture has been wrapped to maintain the curved configuration of the tip of the drainage catheter, unwrapping of the suture can be difficult and time consuming.

Furthermore, when the practitioner releases the suture, the flexible tip on the conventional catheter will not fully release in a manner that allows manipulation of the catheter tip into a substantially straight position. This can be due to a variety of factors. For example, if the drainage catheter is in the patient's body for an extended period of time, the bodily fluids or articles and materials associated with the bodily fluids may encrust the suture thread preventing release of the curved configuration of the tip of the drainage catheter. This can cause the suture to remain in a tensile configuration even after the practitioner has, for example, unwrapped the suture about the handle. Thus, a practitioner may need to perform additional procedures, such as invasive surgery, to remove the catheter.

BRIEF SUMMARY OF THE INVENTION

The present invention relates to systems and apparatus for draining bodily fluid from a patient. In particular, the present invention relates to drainage catheters, and more specifically, to a drainage catheter hub apparatus for selectively securing or releasing a suture.

According to the present invention the drainage catheter hub includes a bistable locking mechanism for securing a suture. In one embodiment, the bistable locking mechanism facilitates convenient securement of the suture which in turn facilitates retention of the catheter within a patient's body. The bistable locking mechanism allows convenient releasing of the suture to facilitate repositioning of the catheter in the patient's body and removal of the catheter from the patient's body, in a safe and convenient manner. In one exemplary embodiment, the drainage catheter comprises a hub having a bistable locking mechanism positioned therein. The bistable locking mechanism can include: (i) an elongate member; (ii) a ball joint component member; and (iii) a socket component member.

The present invention also relates to a release mechanism which reliably enables a drainage tip of the catheter to relax allowing the tip of the catheter to be removed from or repositioned within the patient's body. In one embodiment of the present invention, a suture extends from within the hub, through a portion of the bistable locking mechanism, along the length of the catheter tube, exits through the catheter tip, and is secured to and terminates at a securing wire at an attachment point on the distal portion of the tube. When the bistable lock is in an unlocked configuration, a practitioner can pull the proximal end of the suture to cause the drainage tip to flex toward the tube in a substantially curved fashion. The practitioner can then depress the bistable locking mechanism into a locked configuration to secure the suture inside the bistable locking mechanism. Securing the suture facilitates retention of the drainage tip in the looped or curved configuration. Bodily fluid then enters the drainage tip, travels through the tube, and exits through a proximal portion of the tube.

When repositioning of the catheter is required the practitioner can displace the bistable locking mechanism into an unlocked or relaxed first position, such that the suture is no longer secured. The relaxed suture thus allows for straightening of the drainage tip of the catheter tube to allow the practitioner to reposition the catheter. Once the catheter is appropriately repositioned, the practitioner can return the bistable locking mechanism back to the locked position to effectively retain the position of the catheter in the patient.

Upon completion of the procedure, the practitioner can manipulate the bistable locking mechanism into the unlocked first position thus relaxing the suture. Alternatively, the practitioner can remove the securing wire to disengage the suture from the attachment point on the distal portion of the tube. Thus, the drainage tip of the catheter tube can be straightened prior to removal by either relaxing the suture or removing the securing wire from the catheter.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1A is a perspective view of a drainage catheter having a bistable locking mechanism illustrating a distal end of a catheter tube in a relaxed position;

FIG. 1B illustrates the drainage catheter of FIG. 1A with the distal end of the catheter tube in a tensile configuration;

DETAILED DESCRIPTION OF THE PREFERRED EMBODIMENTS

Figure 2A:
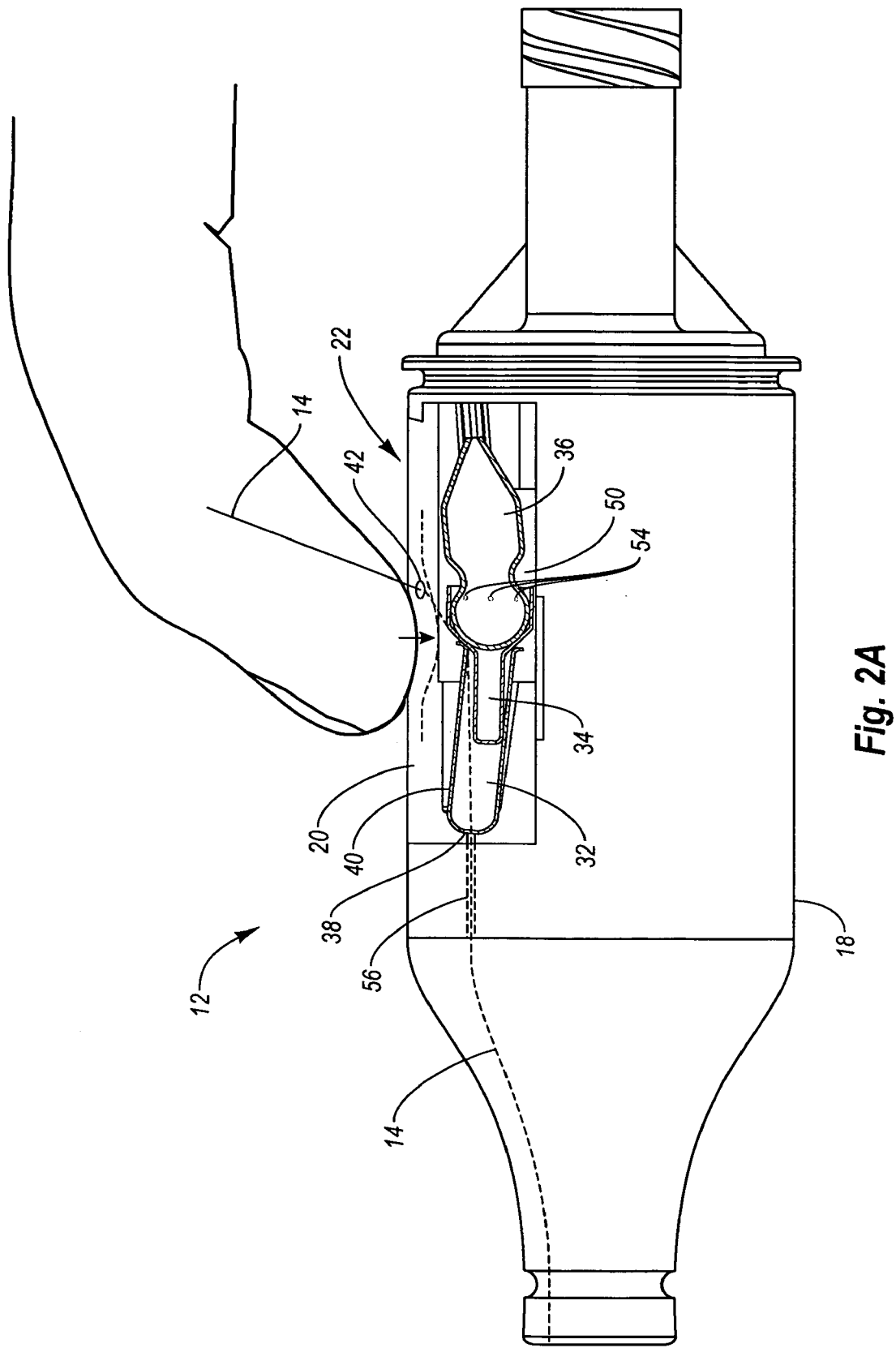
FIG. 2A is a side view of the catheter hub illustrating the components of the bistable locking mechanism when the bistable locking mechanism is in a locked position.

The present invention relates to a drainage catheter having a three-part bistable locking mechanism positioned within the hub of the catheter for securing a suture. The bistable locking mechanism facilitates convenient securement of the suture, which in turn facilitates retention of the catheter within a patient's body. The bistable locking mechanism is also adapted to provide convenient releasing of the suture to facilitate: (i) management of the position of the catheter once it is inserted into the patient's body; and (ii) removal of the catheter from a patient's body, in a safe and convenient manner. In one exemplary embodiment, the drainage catheter comprises a hub having a bistable locking mechanism positioned within the housing of the hub. The bistable locking mechanism is configured to selectively secure and release a suture that is positioned adjacent or within a portion of the bistable locking mechanism. The bistable locking mechanism is adapted to have two equilibriums, one at an unlocked first position which allows movement of the suture, and another at a locked second position which minimizes axial movement of the suture.

FIG. 1A illustrates a drainage catheter 10 having a catheter hub 12 for providing selective securement and releasing of a suture 14. In the illustrated embodiment, drainage catheter 10 includes: (i) a catheter tube 16; (ii) catheter hub 12 coupled to catheter tube 16; and (iii) suture 14. Catheter hub 12 includes: (i) a housing 18; (ii) a resilient outer layer 20 coupled to housing 18; and (iii) a three-part bistable locking mechanism 22 positioned within housing 18. Bistable locking mechanism 22 and its position within housing 18 allow the user to selectively secure and release suture 14. Bistable locking mechanism 22 provides a convenient and efficient mechanism for securing suture 14 to allow a practitioner to safely and effectively manage the position of catheter tube 16 within the patient's body. Likewise, the position of bistable locking mechanism 22 within housing 18 provides for convenient access and manipulation of bistable locking mechanism 22 by the user.

In the illustrated embodiment, bistable locking mechanism 22 is configured to include two equilibrium positions, one at an unlocked first position and another at a locked second position. The configuration of bistable locking mechanism 22 allows a user to toggle between the equilibrium positions. In the equilibrium positions, the configuration of the bistable locking mechanism 22 is maintained until acted upon by an external force. This allows the bistable locking mechanism to maintain an equilibrium position without the assistance of a user. In the first position, bistable locking mechanism 22 allows movement of suture 14. In the second position, bistable locking mechanism 22 minimizes and/or controls axial movement of suture 14. The operation of the first and second positions with respect to performance of drainage catheter 10 will be discussed more fully herein below. FIGS. 1A and 1B illustrate bistable locking mechanism 22 in a first position and second position, respectively. Therefore, bistable locking mechanism 22 provides for releasing of suture 14 when bistable locking mechanism 22 is in the first position (FIG. 1A), and securement of suture 14 when bistable locking mechanism 22 is in the second position (FIG. 1B).

In the illustrated embodiment, resilient outer layer 20 is coupled to housing 18 in a manner to provide a covering to bistable locking mechanism 22. Resilient outer layer 20 is configured to facilitate actuation of bistable locking mechanism 22 between the first and second positions. In the illustrated embodiment, resilient outer layer 20 includes: (i) a recess 40; (ii) a channel 42 configured to accommodated suture 14 therein; and (iii) a depressible button 50. The recess 40 is configured to receive at least a portion of bistable locking mechanism 22 therewithin. Depressible button 50 is adapted to facilitate movement of bistable locking mechanism 22 from the second position to the first position.

In the illustrated embodiment, catheter tube 16 has a proximal end 24 and a distal end 26. Distal end 26 is configured to allow passage of fluids from the exterior of the catheter tube 16 to the main lumen of the catheter tube. Distal end 26 includes: (i) a plurality of drainage bores 28; and (ii) a suture aperture 30. Plurality of drainage bores 28 are positioned on catheter tube 16 between the distal end 26 and proximal ends 24 and are oriented on catheter tube 16 in a substantially linear fashion. Plurality of drainage bores 28 are in fluid communication with the proximal end 24 of catheter tube 26 such that fluid received by plurality of drainage bores 28 can flow to the proximal end 24 of catheter tube 16 in a substantially unobstructed manner.

In the illustrated embodiment, suture 14 is positioned within a portion of catheter hub 12, extends along the length of catheter tube 16, exits catheter tube 16 at a suture aperture 30 and terminates at a connection or attachment point 46 on the distal end 26 of catheter tube 16. In the illustrated embodiment, the end of suture 14 is connected to a stylet 44 near the distal end 26 of catheter tube 16. In another embodiment, one end of suture 14 is connected to the distal end 26 of catheter tube 16. The positioning of suture 14 allows a user to manipulate the shape of the distal end 26 of catheter tube 16 by tensioning or relaxing suture 14. In another embodiment, the suture exits the distal end 26 of the catheter tube 16 and is secured to a position proximal to the tip of the catheter tube 16.

As illustrated in FIG. 1A, catheter tube 16 and suture 14 are in a relaxed state when bistable locking mechanism 22 is in the first position. The distal end 26 of catheter tube 16 is depicted as being straightened for the sake of clarity and to more clearly describe the invention. When the distal end 26 of catheter tube 16 is in a relaxed state it can be straightened for insertion or withdrawal from the patient. However, the natural conformation of distal end 26 of catheter tube 16 can bent or curled, as with typical drainage catheters, such as to require manipulation to achieve the straightened conformation depicted in FIG. 1A. In one embodiment, the relaxed state of catheter tube 16 and suture 14 allows the distal end 26 of catheter tube 16 to be substantially straight relative to the proximal end 24 of catheter tube 16. Pulling suture 14 causes the tip of catheter tube 16 to flex toward the stem of catheter tube 16 in a substantially curved fashion. The curved orientation of the distal end 26 of the catheter tube 16 facilitates retention of drainage catheter 10 within the patient's body.

Where the distal end 26 of catheter tube 16 has a naturally curved configuration when catheter tube 16 and suture 14 are in a relaxed state, the application of tension on suture 14 enhances and helps maintain the curved configuration. This helps prevent the drainage catheter from accidentally being pulled from the patient's body. Further, the distal end 26 of catheter tube 16 is forced into a straight configuration only as it is withdrawn from the patient's body. Nevertheless, when suture 14 and catheter tube 16 are in the relaxed state drainage catheter 10 can be safely and effectively repositioned within the patient's body or removed from the patient's body.

The distal end 26 of catheter tube 16 can comprise any type of material that provides flexible resilience, such as natural or synthetic rubber, flexible plastic, and so forth. Also, the suture 14, as described in the present Figures, can comprise any materials that can be pulled, released, tensed, or relaxed, such as natural or synthetic fibers wound into a string, and so forth, with sufficient tensile strength and resilience to minimize elongation or plastic deformation when under typical tensile strain.

FIG. 1B illustrates drainage catheter in a tensile state. The tensile state is created when the user retracts suture 14 in a rearward direction causing the tip of catheter tube 16 to flex toward catheter tube 16 in a substantially curved fashion. Once the curved orientation is achieved, the user can manipulate bistable locking mechanism 22 to the second position to secure suture 14, and thus maintain the curved orientation of catheter tube 16. When the catheter tube is secured in the curved orientation through utilization of the bistable locking mechanism, accidental removal from a patient's body is controlled because the curvature blocks the drainage catheter from being pulled from the patient's body.

FIG. 2A illustrates a close-up view of catheter hub 12 and bistable locking mechanism 22. Bistable locking mechanism 22 includes: (i) an elongate member 32; (ii) a ball joint component member 36; and (iii) a socket component member 34. In the illustrated embodiment, elongate member 32 is substantially cylindrical having a closed rounded first end that includes an aperture 38 therein, and an open opposing second end having an outwardly extending lip. The elongate member 32 is positionable within recess 40 of resilient outer layer 20 with the rounded first end of elongate member 32 being in pivotal contact with a surface of resilient outer layer 20. Ball joint component member 36 includes a first end in contact with at least one of resilient outer layer 40 and/or housing 18, and a second end comprising a rounded component.

In one embodiment, the first end of ball joint component member is pivotally linked to a surface of housing, and in another embodiment the first end of ball joint component member is pivotally linked to a surface (not shown) of resilient outer layer. In yet another embodiment, the first end of ball joint component member is slidably linked to a surface of the housing, or in the alternative, a surface of the resilient outer layer.

Socket component member 34 includes a first end configured to be received within the second end of elongate member 32 and to be cooperatively engaged therewith. Socket component member 34 also includes a second end comprising a socket configured to receive and pivotally retain the rounded component of ball joint component member 36. The inner surface of the socket includes a plurality of uniform nipples 54 positioned radially therein to facilitate retention of the rounded component of ball joint component member 36 within the socket of socket component member 34. The general shape of the socket also facilitates retention of the rounded component of ball joint component member 36 therein.

In the preferred embodiment, the configuration of bistable locking mechanism 22 and its association with housing 18 and resilient outer layer 20 allow bistable locking mechanism 22 to have an equilibrium in both the first position and the second position. The equilibrium positions allow the respective orientation of the three components of bistable locking mechanism 22 to remain unchanged absent the exertion of an external force on bistable locking mechanism 22 sufficient to reorient bistable locking mechanism 22 to an alternative position, such as from a first position to a second position.

The contact between the rounded first end of elongate member 32 and resilient outer layer 20 provides sufficient flexibility: (i) to retain components of bistable locking mechanism 22 in a linked fashion; and (ii) to provide the necessary force on the components of bistable locking mechanism 22 to retain their orientation in either the first position or the second position. In an alternative embodiment, the rounded first end of elongate member 32 is pivotally linked to housing 18, and at least a portion of at least one of elongate member 32, socket component member 34, and ball joint component member 36 comprise a resilient material sufficient to allow deflection of the resilient member to reorient bistable locking mechanism 22 between the first and second positions when a sufficient force is exerted on bistable locking mechanism 22. In yet another embodiment, the rounded first end of elongate member 32 is linked to housing 18 and the first end of ball joint component member 36 is linked to a surface of resilient outer layer 20.

As shown in FIG. 2A, a user's finger has depressed the bistable locking mechanism 22 using vertical force above the flexibly resilient outer layer 20, so that the bistable locking mechanism 22 is in the second position. The resilient outer layer 20 can comprise any natural or synthetic flexibly resilient materials including resilient metals, metal alloys, resilient rubbers or plastics, and so forth. In the illustrated embodiment, the flexibility of the resilient outer layer 20 facilitates movement of the bistable locking mechanism 22 from the first position to the second position.

Figure 2B:
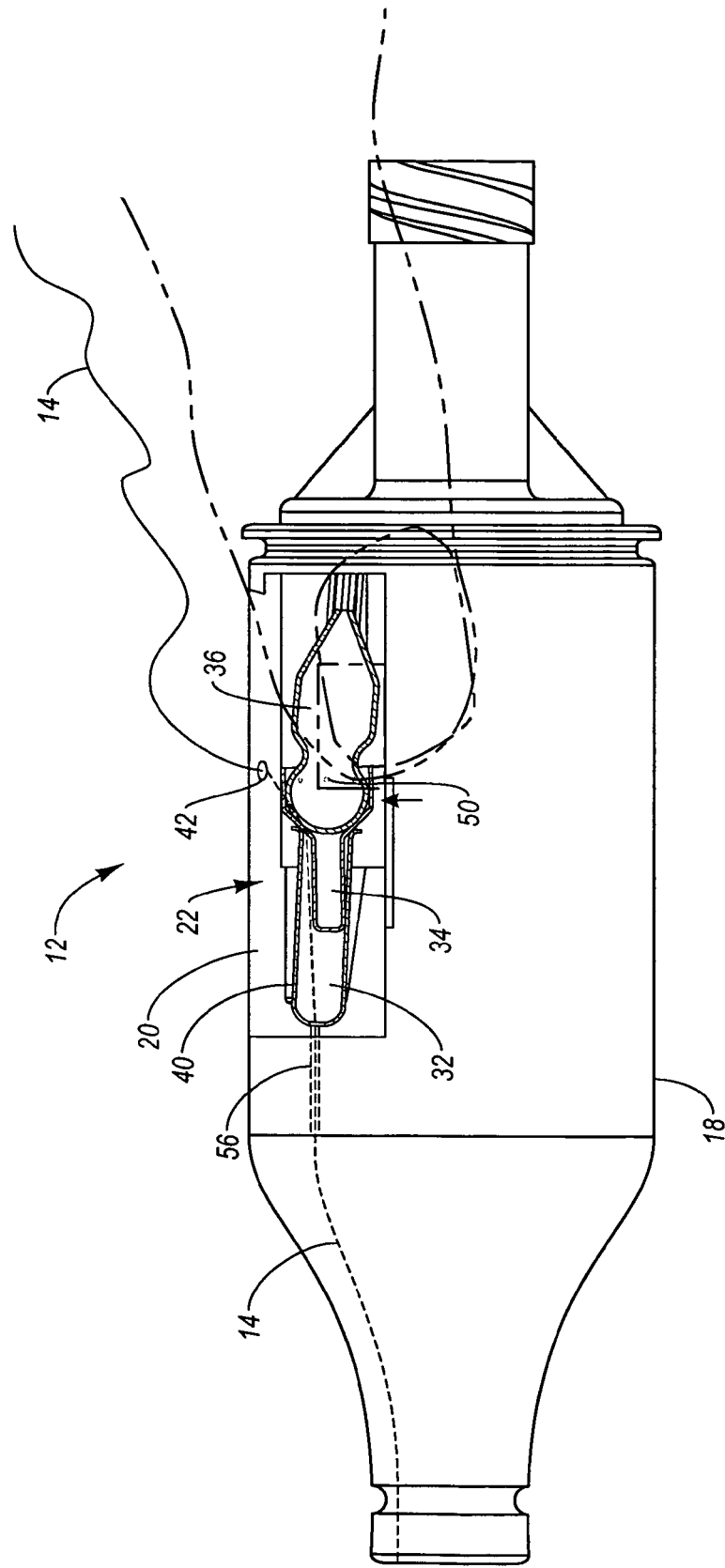
FIG. 2B is a side view of the catheter hub illustrating the components of the bistable locking mechanism when the bistable locking mechanism is in an unlocked position.

As can be further appreciated from FIGS. 2A and 2B, the components 32, 34, and 36 of the bistable locking mechanism 22 cooperate to secure or release the suture 14. In particular, FIGS. 2A-2B shows that suture 14 enters hub 12 from tube 16 of catheter 10 through a channel 56 in housing 18, then enters elongate member 32 through aperture 38. Suture 14 then exits elongate member 32 through the open second end of elongate member 32 such that suture 14 can be contacted by a surface on socket component member 34. Suture 14 then extends through opening 42 of resilient outer layer 20.

In the illustrated embodiment, suture 14 is positioned between an inner surface of elongate member 32 and an outer surface of socket component member 34 such that when bistable locking mechanism 22 is in the second position the suture 14 is securely retained in position by elongate member 32 and socket component member 34. When in the second position, the relative orientation of elongate member 32 and socket component member 34 are such that suture 14 is sandwiched between a portion of the inner surface of elongate member 32 and a portion of the outer surface of socket component member 34 to effectively secure suture 14 from axial movement. Conversely, when bistable locking mechanism 22 is in the first position as shown in FIG. 2B, the relative orientation of elongate member 32 and socket component member 34 allows suture 14 to be sufficiently free to slide relative to the components of bistable locking mechanism 22.

FIG. 2B illustrates the catheter hub 12 of FIG. 2A with bistable locking mechanism 22 being in a first position. Bistable locking mechanism 22 can be moved to the first position by applying force to resilient depressible button 50 to move bistable locking mechanism 22 to an upward conformation. Resilient depressible button 50 is coupled to resilient outer layer 20 and positioned adjacent to ball joint component member 36. As shown in FIG. 2B, resilient button 50 is positioned such that depressing resilient button 50 toward bistable locking mechanism 22 causes ball joint component member 36 to shift upward into a raised, or unlocked, orientation, or in other words to the first position. In general, the resilient button 50 may comprise any flexibly resilient materials, such as those also described herein for the outer layer 20, which allow a user to apply pressure directly to the bistable locking mechanism 22. As such, pressure applied to the resilient button 50 causes the bistable locking mechanism 22 to shift from the second position to the first position.

As will be appreciated by those skilled in the art, a variety of types and configurations of bistable mechanisms can be utilized without departing from the scope and spirit of the present invention. For example, in one embodiment, the bistable mechanism secures the suture when in an upward conformation and allows movement of the suture when in a downward conformation. In another embodiment, the bistable mechanism is comprised of two primary members. In another embodiment, the bistable mechanism is comprised of more than three primary members. In yet another embodiment, the bistable mechanism allows for locking or releasing of a secondary component separate from the bistable mechanism. In another embodiment, the bistable mechanism moves side to side rather than up and down.

Figure 3:
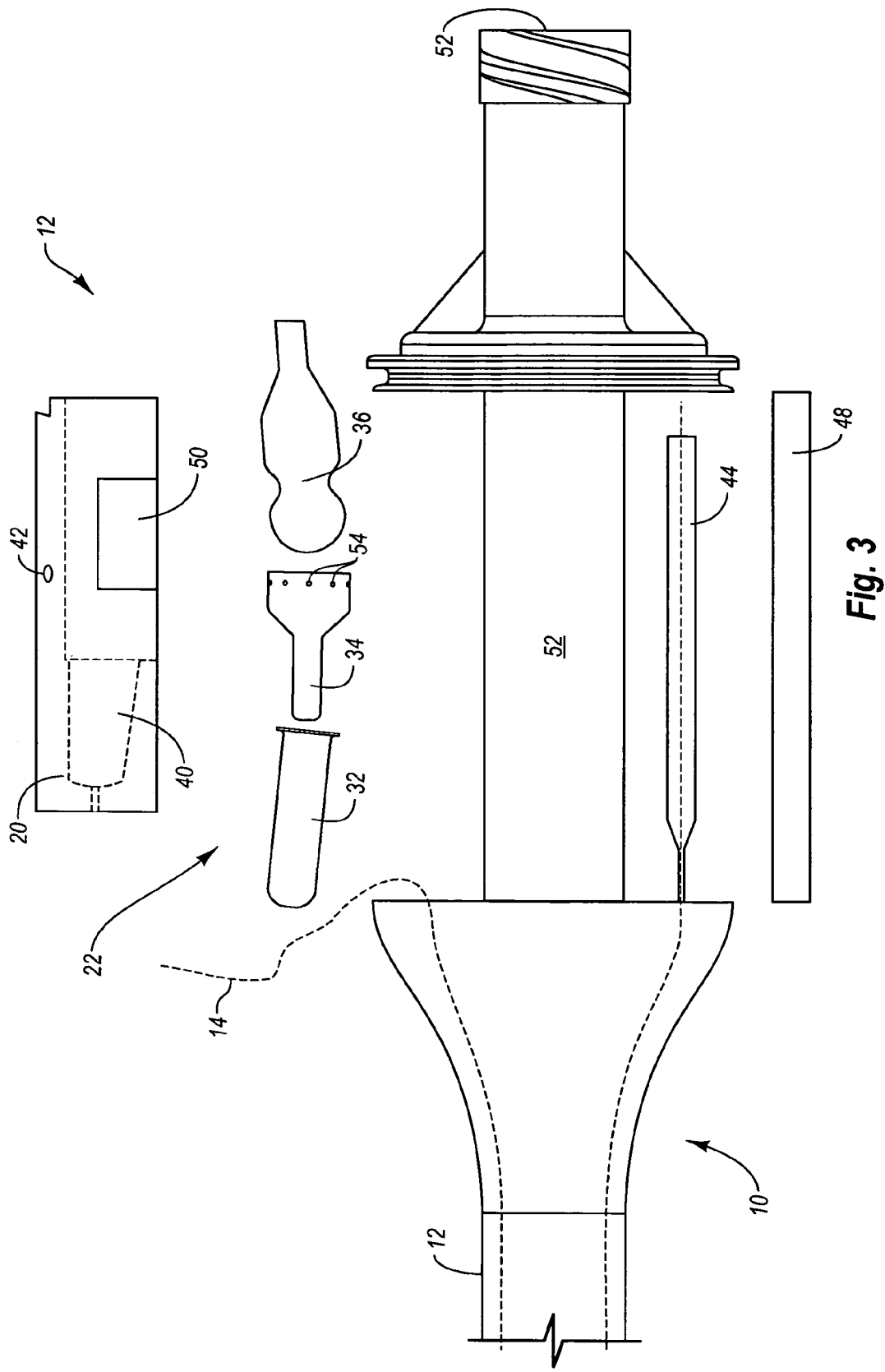
FIG. 3 is an exploded view of the catheter hub illustrating the components of the bistable locking mechanism.

FIG. 3 illustrates an exploded view of catheter hub 12 and the corresponding components of bistable locking mechanism 22. As illustrated in FIG. 3, drainage catheter hub 12 comprises an inner lumen 52 that extends from tube 16 (See FIG. 1) through to the proximal end of catheter hub 12. Bistable locking mechanism 22 is positioned above inner lumen 52. Bistable locking mechanism comprises, elongate member 32, socket component member 34, and ball joint component member 36 positioned in a cooperative manner, as previously described. Resilient outer layer 20 envelopes bistable locking mechanism 22 to facilitate movement of bistable locking mechanism 22 between the first and second positions. In the illustrated embodiment, resilient outer layer includes depressible button 50 which can be utilized to facilitate movement of bistable locking mechanism 22 from the second position to the first position.

FIG. 3 further illustrates a channel for containing stylet 44. In at least one embodiment, stylet 44 extends from hub 12, along tube 16, to the attachment point 46 at the distal end 26 of catheter 16 (See FIG. 1). Stylet 44 can comprise a memory material, such as Nitinol wire, and operates as an attachment interface for suture 14. Stylet 44 can be pulled in a proximal direction, to facilitate detachment of suture 14 from stylet 44, and allow distal end 26 of catheter 10 to relax and be manipulated to a substantially straight conformation.

In the illustrated embodiment, a removable lower cap 48 is provided in connection with stylet 44. Removable lower cap 48 is fixed to hub 12 in either a hinged, or snap-fit manner. Stylet 44 is secured to removable lower cap 48 such that the user can retract stylet 44 by removing or dropping the lower cap 48 with respect to the hub 12. As the user pulls the lower cap 48 in a rearward direction, thus retracting stylet 44 in a rearward direction, the suture 14 is released and the catheter tip is relaxed. As such, the stylet 44 can provide a convenient redundant measure for relaxing the suture 14 to allow removal of catheter 10 from the patient's body.

For example, as will be understood from the corresponding Figures, the drainage catheter in accordance with the present invention has been described in two conformations: a relaxed conformation, and a tensile conformation. In the relaxed conformation (e.g., FIG. 1A), the drainage catheter can be straightened, and conforms primarily along one axis from a proximal end to a distal end of the catheter. In general, the relaxed conformation is preferable for inserting, repositioning and removing the drainage catheter into, within and from the patient's body, respectively. By contrast, the tensile conformation (e.g., FIG. 1B) is generally preferable for draining bodily fluid. For example, in the tensile conformation, the distal end of the drainage catheter is flexed toward the tube of the drainage catheter, due to a tensioning of the suture. The flexed or curved orientation helps to retain the catheter within the patient's body.

To insert the drainage catheter 10 into a patient, a practitioner inserts the distal end 26 of the drainage catheter 10, while in the relaxed, substantially straightened configuration, into an appropriate bodily tissue or cavity where excess fluid may exist. Once in the appropriate position, the practitioner then tensions the suture 14, causing the distal end 26 to flex inwardly toward the tube 16 (FIG. 1B). Bodily fluid can then flow through drainage bores 28 of the tube 16 into the main lumen of drainage catheter 10 out through a lumen 52 of the catheter hub. To hold the tension of the suture 14, and hence the conformation of the distal end 26 relative to the tube 16 the bistable locking mechanism 22 can be manipulated into the second position (as shown in FIG. 1B). In this engaged, or locked, orientation (i.e., the second position) the suture 14 is effectively prohibited from moving in either a proximal or a distal direction along the tube 16 and drainage tip 14.

The user, however, can move the bistable locking mechanism to the first position to release the suture 14 when repositioning of the catheter is desired or after drainage has completed. For example, as has been explained, a practitioner can depress the button 50 inward toward the bistable locking mechanism 22, causing the bistable locking mechanism 22 to toggle from the depressed orientation to the raised orientation, or in other words from the second position to the first position. When the hub 12 becomes unlocked in this manner, the suture 14 will naturally relax, allowing the distal end 26 to relax and be manipulated into a substantially straight conformation. The relaxed orientation allows the user to: (i) manage the position of the catheter within patient's body by repositioning the catheter to an appropriate position; and (ii) removing the catheter from the patient's body, in a safe and effective manner. Thus, the present invention allows a practitioner to conveniently and reliably secure or release the drainage tip 14 relative to the tube 16, to selectively maintain or release the tension at the hub 12.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A drainage catheter hub for use in connection with a drainage catheter to receive and secure a suture therein, the drainage catheter for use in providing a fluid pathway for draining bodily fluid from a cavity or tissue of a patient, the drainage catheter being configured such that the suture is utilized in connection with the drainage catheter to selectively secure a distal end of the catheter in an anchor configuration, the drainage catheter hub comprising:
    a housing having a channel to accommodate a suture;
    a bistable locking mechanism positioned in the housing and being adapted to provide selective securement of the suture, wherein the bistable locking mechanism allows movement of the suture when the bistable locking mechanism is in a first position, and wherein the bistable locking mechanism secures the suture to minimize movement of the suture when the bistable locking mechanism is in a second position, the bistable locking mechanism comprising:
        an elongate member having a first end;
        a ball joint component member, having an end comprising a rounded component; and
        a socket component member positioned between the elongate member and the ball joint component member, the socket component member having an elongate first end positioned within the elongate member and a second end forming a socket to receive and retain the rounded component of the ball joint component member, wherein the suture is threaded through the elongate member and runs along the outside surface of the elongate first end of the socket component member such that the suture is securely sandwiched between the inner portion of the elongate member and the outside surface of the elongate first end of the socket component member to securely retain the suture when the bistable locking mechanism is in a second position and wherein the suture is threaded through the elongate member and runs along the outside surface of the elongate first end of the component member such that the suture is movably positioned between the inner portion of the elongate member and outside surface of the elongate first end of the socket component member to allow movement of the suture when the bistable locking member is in a second position; and
    a resilient outer layer utilized in connection with the bistable locking mechanism and coupled to the housing, the resilient outer layer adapted to allow the user to actuate the bistable locking mechanism between the first position and the second position to selectively secure and release the suture.

2. The drainage catheter as recited in claim 1, wherein the bistable locking mechanism is configured to pinch the suture when in the second position, and to release the suture when in the first position.

3. The drainage catheter as recited in claim 1, further comprising a depressible button positioned about the outer resilient layer, wherein the depressible button is configured to allow shifting of the bistable locking mechanism from the second position into the first position.

4. The drainage catheter as recited in claim 1, further comprising a securing wire, wherein the securing wire comprises a memory material.

5. A drainage catheter hub for use in connection with a drainage catheter to receive and secure a suture therein, the drainage catheter for use in providing a fluid pathway for draining bodily fluid from a cavity or tissue of a patient, the drainage catheter being configured such that the suture is utilized in connection with the drainage catheter to selectively secure a distal end of the catheter in an anchor configuration, the drainage catheter hub comprising:
    a housing having a channel to accommodate a suture;
    a bistable locking mechanism positioned in the housing and being adapted to provide selective securement of the suture, wherein the bistable locking mechanism allows movement of the suture when the bistable locking mechanism is in a first position, and wherein the bistable locking mechanism secures the suture to minimize movement of the suture when the bistable locking mechanism is in a second position; and
    a resilient outer layer utilized in connection with the bistable locking mechanism and coupled to the housing, the resilient outer layer adapted to allow the user to actuate the bistable locking mechanism between the first position and the second position to selectively secure and release the suture;
    a securing wire, wherein the securing wire comprises a memory material; and
    a removable lower cap positioned about the hub, wherein the lower cap is configured to provide a user with access to the securing wire when the lower cap is removed.

6. A drainage catheter hub for use in a drainage catheter to allow selective securement of a suture therein, the hub comprising:
    a housing having a channel to accommodate a suture;
    a resilient outer layer coupled to the housing; and
    a bistable locking mechanism positioned within the housing and utilized in connection with the resilient outer layer to provide selective securement of the suture, wherein the bistable locking mechanism allows movement of the suture when the bistable locking mechanism is in a first position, and wherein the bistable locking mechanism is adapted to minimize distal movement of the suture when the bistable locking mechanism is in a second position, the bistable locking mechanism comprising:
        an elongate member having a first end abutting a surface of the resilient outer layer and an opposing second end;
        a ball joint component member having a first end abutting one of the housing and the resilient outer layer, and a second end comprising a rounded component; and
        a socket component member positioned between the elongate member and the ball joint component member, the socket component member having an elongate first end positioned within the second end of the elongate member, and a second end forming a socket configured to receive and retain the rounded component of the ball joint component member wherein the suture is threaded through the elongate member and runs along the outside surface of the elongate first end of the socket component member such that the suture is securely sandwiched between the inner portion of the elongate member and the outside surface of the elongate first end of the socket component member to securely retain the suture when the bistable locking mechanism is in a second position and wherein the suture is threaded through the elongate member and runs along the outside surface of the elongate first end of the component member such that the suture is movably positioned between the inner portion of the elongate member and outside surface of the elongate first end of the socket component member to allow movement of the suture when the bistable locking member is in a second position.

7. The hub as recited in claim 6, further comprising a resilient outer layer adapted to allow a user to actuate the bistable locking mechanism between the first position and the second position to selectively secure and release the suture wherein the resilient outer layer comprises a channel to accommodate the suture, and wherein the elongate member comprises an aperture positioned within the first end of the elongate member to accommodate the suture.

8. The hub as recited in claim 7, wherein the suture is positioned within the channel of the housing, through the aperture of the elongate member, out through the second end of the elongate member, and then out through the channel of the resilient outer layer.

9. The drainage catheter as recited in claim 6, further comprising a depressible button positioned about the outer resilient layer, wherein the depressible button is configured to facilitate movement of the bistable locking mechanism from the second position to the first position.

10. The drainage catheter as recited in claim 6, wherein the outer resilient layer is configured to allow a user to move the bistable locking mechanism from the first position into the second position by applying pressure to at least a portion of the outer resilient member.

11. The drainage catheter as recited in claim 6, further comprising a securing wire, wherein the securing wire comprises a memory material.

12. A drainage catheter hub for use in a drainage catheter to allow selective securement of a suture therein, the hub comprising:
a housing having a channel to accommodate a suture;
a resilient outer layer coupled to the housing; and
a bistable locking mechanism positioned within the housing and utilized in connection with the resilient outer layer to provide selective securement of the suture, wherein the bistable locking mechanism allows movement of the suture when the bistable locking mechanism is in a first position, and wherein the bistable locking mechanism is adapted to minimize distal movement of the suture when the bistable locking mechanism is in a second position, the bistable locking mechanism comprising:
an elongate member having a first end abutting a surface of the resilient outer layer and an opposing second end;
a ball joint component member having a first end abutting one of the housing and the resilient outer layer, and a second end comprising a rounded component; and
a socket component member positioned between the elongate member and the ball joint component member, the socket component member having a first end configured to cooperatively engage the second end of the elongate member, and a second end forming a socket configured to receive and retain the rounded component of the ball joint component member;
a securing wire, wherein the securing wire comprises a memory material; and
a removable lower cap positioned about the hub, wherein the lower cap is configured to provide a user with access to the securing wire when the lower cap is removed.

13. A drainage catheter hub for use in a drainage catheter to allow selective securement of a suture therein, the hub comprising:
a housing having a channel to accommodate a suture;
a resilient outer layer coupled to the housing, the resilient outer layer having a channel to accommodate the suture; and
a three-part bistable locking mechanism positioned within the housing and covered by the resilient outer layer to provide selective securement of the suture, wherein the bistable locking mechanism allows movement of the suture when the bistable locking mechanism is in a first position, and wherein the bistable locking mechanism is adapted to minimize distal movement of the suture when the bistable locking mechanism is in a second position, the three-part bistable locking mechanism comprising:
a hollow elongate member having a first rounded end with an aperture positioned therein, and an opposing second end having an opening in communication with the aperture, wherein the first rounded end is in contact with a portion of the resilient outer layer;
a ball joint component member having a first end abutting one of the housing and the resilient outer layer, and a second end comprising a rounded component; and
a socket component member positioned between and linked to the elongate member and the ball joint component member to form the bistable locking mechanism, the socket component member having a first end configured to be received within the opening of the second end of the hollow elongate member, and a second end forming a socket configured to receive and pivotally retain the rounded component of the ball joint component member,
such that the suture extends from the aperture of the hollow elongate member is threaded through the length of the elongate member, the suture being positioned between the inner portion of the elongate member and the outside surface of the first end of the socket component member, such that the suture can move relative to the elongate hollow member when the bistable locking mechanism is in the first position and the suture is secured from distal movement when the bistable locking mechanism is in a second position.

14. A drainage catheter for use in providing a fluid pathway for draining bodily fluid from a cavity or tissue of a patient, the drainage catheter being configured such that a suture is utilized in connection with the drainage catheter to selectively secure a distal end of the catheter in an anchor configuration, the drainage catheter comprising:
a catheter tube having a distal end for receiving fluid, and a proximal end for dispersing fluid received from the distal end;
a suture extending along the catheter tube, and being secured at an attachment point to secure the distal end of the catheter tube in an anchor configuration; and
a catheter hub coupled to the catheter tube, the hub configured to receive and secure the suture therein, the hub comprising:

a housing having a channel to accommodate the suture;
a bistable locking mechanism positioned in the housing to provide selective securement of the suture, the bistable locking mechanism comprising:
  an elongate member having a first end;
  a ball joint component member, having an end comprising a rounded component; and
  a socket component member positioned between the elongate member and the ball joint component member, the socket component member having an elongate first end positioned within the elongate member and a second end forming a socket to receive and retain the rounded component of the ball joint component member, wherein the suture is threaded through the elongate member and runs along the outside surface of the elongate first end of the socket component member such that the suture is securely sandwiched between the inner portion of the elongate member and the outside surface of the elongate first end of the socket component member when the bistable locking mechanism is in a second position and wherein the suture is threaded through the elongate member and runs along the outside surface of the elongate first end of the component member such that the suture is movably positioned between the inner portion of the elongate member and outside surface of the elongate first end of the socket component member when the bistable locking member is in a second position such that the bistable locking mechanism is configured to (i) allow movement of the suture when the bistable locking mechanism is in the first position, and (ii) minimize distal movement of the suture when the bistable locking mechanism is in the second position, wherein the configuration of the bistable locking mechanism biases the bistable locking mechanism to either the first position or the second position; and
a resilient outer layer utilized in connection with the bistable locking mechanism and coupled to the housing to facilitate selective securement of the suture, wherein the resilient outer layer is adapted to allow a user to toggle the bistable locking mechanism between the first and second positions so selectively secure and release the suture.

* * * * *